United States Patent [19]

Wade

[11] Patent Number: 4,507,477

[45] Date of Patent: Mar. 26, 1985

[54] PROCESS FOR TETRAZOLYL-PYRIMIDINONE DERIVATIVES

[75] Inventor: James J. Wade, Oakdale, Minn.

[73] Assignee: Riker Laboratories, Inc., St. Paul, Minn.

[21] Appl. No.: 416,272

[22] Filed: Sep. 9, 1982

[51] Int. Cl.³ .................. C07D 498/04; C07D 513/04
[52] U.S. Cl. ..................................... 544/250; 544/278
[58] Field of Search ................ 544/278, 250; 542/414, 542/422

[56] References Cited

U.S. PATENT DOCUMENTS

| | | | |
|---|---|---|---|
| 3,585,198 | 6/1971 | Meszaros et al. | 260/251 |
| 3,960,847 | 6/1976 | Yale | 544/282 |
| 4,122,274 | 10/1978 | Juby | 544/282 |
| 4,209,620 | 6/1980 | Juby | 544/252 |
| 4,223,031 | 9/1980 | Covington et al. | 424/251 |
| 4,232,024 | 11/1980 | Winter et al. | 424/251 |
| 4,414,388 | 11/1983 | Kadin | 544/48 |

FOREIGN PATENT DOCUMENTS 2519816 10/1976 Fed. Rep. of Germany ...... 544/282

OTHER PUBLICATIONS

Meszaros, et al., Arzneim–Forsch., 22, 815–829, (1972).
Sam and Plampin, J. Pharm. Sci., 53, 538–544, (1964).
Finnegan et al., J. Am. Chem. Soc., 80, 3908–3911, (1958).
Yevich et al., J. Med. Chem., 25, 864–868, (1982), (Jul. issue).

Primary Examiner—Donald G. Daus
Assistant Examiner—Diana G. Rivers
Attorney, Agent, or Firm—Donald M. Sell; James A. Smith; Robert W. Sprague

[57] ABSTRACT

A process for preparing compounds of the formula

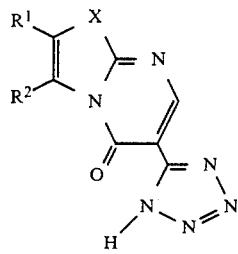

wherein X is sulfur or oxygen; and $R^1$ and $R^2$ are independently selected from the group consisting of H and an alkyl group containing 1 to about 4 carbon atoms, or $R^1$ and $R^2$ are fused to form a benzene ring which is optionally substituted by one or more substituents independently selected from the group consisting of an alkyl group containing 1 to about 4 carbon atoms, an alkoxy group containing 1 to about 4 carbon atoms, and halogen. The process involves reacting together a 2-aminooxazole, 2-aminobenzoxazole, 2-aminothiazole or 2-aminobenzothiazole, an alkyl tetrazol-5-ylacetate, and a trialkyl orthoformate and cyclizing the resulting intermediate.

6 Claims, No Drawings

PROCESS FOR TETRAZOLYL-PYRIMIDINONE DERIVATIVES

FIELD OF THE INVENTION

This invention relates to a novel synthetic process. More specifically, it relates to a process for the preparation of compounds containing a pyrimidinone ring, an oxazole, benzoxazole, thiazole, or benzothiazole ring fused to the pyrimidinone ring, and a tetrazole ring bonded to the pyrimidinone ring at a position alpha to the keto group thereof. Novel intermediates are also included within the scope of the invention.

BACKGROUND OF THE INVENTION

U.S. Pat. No. 4,223,031 describes the antiallergic agents 3-(1H-tetrazol-5-yl)-4H-pyrimido[2,1-b]-benzothiazol-4-ones and 6-(1H-tetrazol-5-yl)thiazolo[3,2-a]-pyrimidin-5-ones and methods for their synthesis. Unfortunately, the synthetic methods described therein generally require several steps and are therefore not particularly convenient.

Sam and Plampin, *J. Pharm. Sci.*, 53,538 (1964) describes the synthesis of substituted 2-aminobenzoxazoles and substituted benzoxazolinones.

Ethyl tetrazol-5-ylacetate is described by Finnegan, et al., *J. Am. Chem. Soc.*, 80,3908 (1958). It is used to prepare 5-phenyltetrazole and various other substituted tetrazoles.

DETAILED DESCRIPTION

The present invention relates to novel processes for preparing compounds of formula I

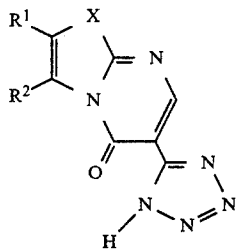

wherein X is sulfur or oxygen; and $R^1$ and $R^2$ are independently selected from the group consisting of H and an alkyl group containing 1 to about 4 carbon atoms, or $R^1$ and $R^2$ are fused to form a benzene ring which is optionally substituted by one or more substituents independently selected from the group consisting of an alkyl group containing 1 to about 4 carbon atoms, an alkoxy group containing 1 to about 4 carbon atoms, and halogen. The preferred halogen substituent is chlorine.

Compounds of formula I are useful antiallergic agents as indicated in U.S. Pat. No. 4,223,031 and copending application Ser. No. 416,243, filed of even date and commonly assigned, both incorporated herein by reference.

A process in accordance with the present invention for the preparation of compounds of Formula I may be illustrated in general terms as follows in Procedure A:

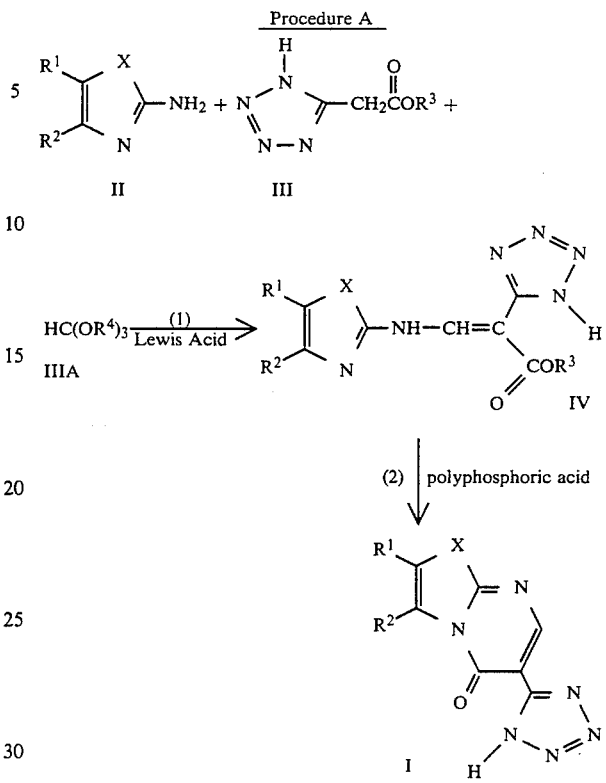

wherein X and $R^1$ and $R^2$ are as previously defined; $R^3$ is an alkyl group containing 1 to about 4 carbon atoms; and each $R^4$ is independently an alkyl group containing 1 to about 4 carbon atoms. Compounds of Formula IV are the novel intermediates of the present invention.

In step (1) of Procedure A, a 2-aminooxazole, 2-aminobenzoxazole, 2-aminothiazole, or 2-aminobenzothiazole of Formula II, an alkyl tetrazol-5-ylacetate of Formula III and a trialkyl orthoformate ester of Formula IIIA are reacted together in the presence of a Lewis acid catalyst. Useful 2-aminoxazoles, 2-aminobenzoxazoles, 2-aminothiazoles, and 2-aminobenzothiazoles are well known to the art. Specific examples of useful 2-aminooxazoles for employment as the amine of Formula II include 2-aminooxazole, 2-amino-4,5-dimethyloxazole and 2-amino-4-chlorooxazole. Specific examples of useful 2-aminobenzoxazoles for employment as the amine of Formula II include 2-aminobenzoxazole, 2-amino-5-chlorobenzoxazole, 2-amino-5-methoxybenzoxazole, 2-amino-6-chlorobenzoxazole, 2-amino-5-methylbenzoxazole, 2-amino-7-chlorobenzoxazole, 2-amino-4-chlorobenzoxazole, 2-amino-6-bromo-5-chlorobenzoxazole, and 2-amino-5,6-dichlorobenzoxazole. Examples of useful 2-aminothiazoles and 2-aminobenzothiazoles for employment as the amine of Formula II are described in said U.S. Pat. No. 4,223,031, incorporated herein by reference. Specific examples of useful 2-aminothiazoles are 2-aminothiazole, 2-amino-4,5-dimethylthiazole, 2-amino-4-methyl-5-bromothiazole, and 2-amino-4-methyl-5-methoxythiazole. Specific examples of useful 2-aminobenzothiazoles are 2-aminobenzothiazole, 2-amino-4-methylbenzothiazole, 2-amino-5-methylthiazole, 2-amino-6-methylbenzothiazole, 2-amino-7-methylbenzothiazole, 2-amino-5,6-dimethoxybenzothiazole, and 2-amino-4-chlorobenzothiazole.

Ethyl tetrazol-5-ylacetate is the preferred alkyl tetrazol-5-ylacetate of Formula III. The mole ratio of alkyl tetrazol-5-ylacetate of Formula III to amine of Formula II is preferably about 1:1.

Examples of suitable trialkyl orthoformate esters of Formula IIIA for employment in step (1) are trimethyl orthoformate and triethyl orthoformate. One mole of trialkyl orthoformate per mole of alkyl tetrazol-5-ylacetate is required to obtain complete reaction. It is preferred that a slight molar excess of the trialkyl orthoformate be employed.

Examples of suitable Lewis acid catalysts for employment in step (1) are zinc chloride, stannous chloride and the like. The preferred catalyst is aluminum trichloride. Weaker acids such as boron trifluoride and p-toluenesulfonic acid generally provide poorer yields in most cases and are not preferred. Catalytic amounts, e.g., less than 30 mole percent, and preferably about 10 mole percent of catalyst, are used.

The reaction of step (1) may be conducted by combining the reactants and heating at about 100° to 150° C. Any volatile distillates may be collected if desired. The reaction of step (1) may be carried out in an inert solvent such as dioxane or trichloroethylene. The novel intermediate of Formula IV may be isolated at this point and purified, or the reaction product of step (1) may be used directly in step (2) without isolation and purification of the intermediate of Formula IV.

In step (2) the intermediate of Formula IV preferably is combined with polyphosphoric acid and heated to effect cyclization to the desired product of Formula I. The mixture is generally heated in the absence of solvent at 100° to 150° C.

An alternative, one-step process in accordance with the present invention may be illustrated in general terms as follows in Procedure B:

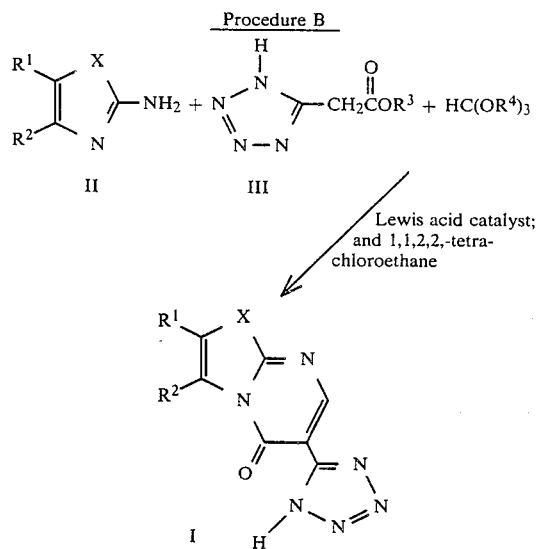

wherein X, $R^1$, $R^2$, $R^3$ and $R^4$ are as defined previously.

In procedure B, reaction of a 2-aminooxazole, 2-aminobenzoxazole, 2-aminothiazole, or 2-aminobenzothiazole of Formula II, an alkyl tetrazol-5-ylacetate of Formula III, and a trialkyl orthoformate of Formula IIIA in the presence of a Lewis acid catalyst and the cyclization of the resulting intermediate to form the compound of Formula I occur sequentially in a one-step process when the indicated 1,1,2,2-tetrachloroethane is employed as the solvent. The reaction mixture is generally heated at about 100° to 150° C., 130° C. being the preferred temperature. Suitable trialkyl orthoformate esters and Lewis acid catalysts include those discussed above in connection with Procedure A.

The final product of either Procedure A or B is readily isolated and purified using conventional methods such as extraction, filtration, recrystallization, and chromatography.

Preferred compounds of Formula I which may be prepared by Procedures A or B of the present invention are of the more specific Formula VII

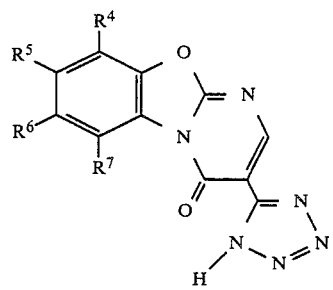

wherein $R^4$, $R^5$, $R^6$ and $R^7$ are each selected independently for the group consisting of hydrogen, an alkyl group containing 1 to about 4 carbon atoms, an alkoxy group containing 1 to about 4 carbon atoms and halogen. Compounds of Formula VII, pharmaceutical compositions containing the compounds of Formula VII, and methods for using compounds of Formula VII in the treatment of allergic conditions are described in said copending application Ser. No. 416,243.

The following examples are provided for the purpose of further illustrating the invention but are not intended to limit the scope thereof in any way.

EXAMPLE 1

Synthesis of 3-(1H-Tetrazol-5-yl)-4H-pyrimido-[2,1-b]benzoxazol-4-one

A mixture of 6.70 g (50.0 mmole) of 2-aminobenzoxazole, 7.8 g (50.0 mmole) of ethyl tetrazol-5-ylacetate and 10.0 g (67.8 mmole) of triethyl orthoformate was heated to 120° C., and 0.3 g of aluminum trichloride was then added thereto. The resulting mixture was maintained at 120° C. for about 40 minutes and cooled and triturated with 20 ml of methanol. The mixture was diluted to 100 ml with ice water. The resulting pale yellow solid was separated by filtration, washed sequentially with water and methanol, and dried to provide 10.89 g (73%) of ethyl 2-[N-(2-benzoxazolyl)amino]-1-(1H-tetrazol-5-yl)acrylate. Infrared and nuclear magnetic resonance spectral analyses were consistent with the structural assignment.

A stirred mixture of 20 g of polyphosphoric acid and 1.00 g (3.33 mmole) of the ethyl 2-[N-(2-benzoxazolyl)-amino]-1-(1H-tetrazol-5-yl)acrylate prepared above was heated gradually until foaming began at about 150° C. Heating and stirring were continued for 25 minutes. The hot mixture was poured into 200 ml of an ice-water mixture. The resulting solid was separated by filtration, washed thoroughly with water, and dried to give 0.44 g (52%) of a pale-yellow solid. The solid was further purified in combination with the product from another run on a 5.00 mmole scale by combining the solids and recrystallizing from a mixture of N,N-dimethylformamide and water (20 ml/5 ml, respectively). The solid was washed twice with 50 ml portions of hot water to provide white solid 3-(1H-tetrazol-5-yl)-4H-pyrimido[2,1-b]benzoxazol-4-one. Analysis: Calculated for $C_{11}H_6N_6O_2$: %C, 52.0; %H, 2.4; %N, 33.1; Found: %C, 52.0; %H, 2.2; %N, 33.1. The structural assignment was confirmed by infrared and nuclear magnetic resonance spectral analyses.

EXAMPLE 2

Synthesis of 3-(1H-Tetrazol-5-yl)-4H-pyrimido[2,1-b]benzothiazol-4-one

To a mixture of 4.5 g (30 mmole) of a 2-aminobenzothiazole, 4.68 g (30 mmole) of ethyl tetrazol-5-ylacetate and 10 g (68 mmole) of triethyl orthoformate was added 0.4 of aluminum trichloride, and the resulting mixture was heated at 110° to 120° C. while collecting the distillate. Once distillation stopped (after about 45 minutes), the mixture was cooled and triturated with ethanol. The resulting yellow solid was separated by filtration, washed with ethanol and dried to provide 8.53 g (90%) of ethyl 2-[N-(2-benzothiazolyl)amino]-1-(1H-tetrazol-5-yl)acrylate. The structure of the product was confirmed by nuclear magnetic resonance spectral analysis.

A stirred mixture of 12 g of polyphosphoric acid and 3.00 g (9.49 mmole) of the ethyl 2-[N-(2-benzothiazolyl)amino]-1-(1H-tetrazol-5-yl)acrylate prepared above was heated gradually to 140° C. At this temperature foaming was observed. Heating and stirring were continued for 15 minutes and the mixture was then allowed to cool to about 20° C. To the mixture was added 100 ml of water, with mixing. The resulting solid was separated by filtration and washed with water. The solid was dried to provide 2.17 g (85%) of light yellow solid 3-(1H-tetrazol-5-yl)-4 H-pyrimido[2,1-b]benzothiazol-4-one. The structure was confirmed by comparison to the infrared spectrum of the known compound.

EXAMPLE 3

Synthesis of 6-(1H-Tetrazol-5-yl)thiazolo-[3,2-a]pyrimidine-5-one

A mixture of 1.00 g (10.0 mmole) of 2-aminothiazole, 1.56 g (10.0 mmole) of ethyl tetrazol-5-ylacetate, 2.00 g (13.5 mmole) of triethyl orthoformate and 0.2 g (1.5 mmole) of aluminum chloride were combined and heated at about 120° C. in an open flask for 30 minutes. The mixture was cooled and triturated with water, and the solid was separated by filtration. The solid was washed sequentially with water and a small amount of methanol to provide 1.95 g (73%) of yellow solid ethyl 2-[N-(2-thiazolyl)amino]-1-(1H-tetrazol-5-yl)acrylate. The structural assignment was confirmed by infrared and nuclear magnetic resonance spectral analyses.

A mixture of 9 g of polyphosphoric acid and 2.00 g (7.52 mmole) of the ethyl 2-[N-(2-thiazolyl)-amino]-1-(1H-tetrazol-5-yl)acrylate prepared above was heated gradually over fifteen minutes to 120° C. and was maintained at that temperature for thirty minutes. To this thick mixture was added, with stirring, 100 ml of an ice-water mixture. The solid was separated by filtration, washed with water and dried to provide 1.52 g (92%) of 6-(1H-tetrazol-5-yl)thiazolo[3,2-a]pyrimidine-5-one. The structure was confirmed by infrared and nuclear magnetic resonance spectral analyses. The product was further purified by washing sequentially with hot N,N-dimethylformamide, hot water, and methanol to provide an off-white solid.

EXAMPLE 4

Alternative Synthesis of 3-(1H-Tetrazol-5-yl)-4H-pyrimido[2,1-b]benzoxazol-4-one A mixture of 1.34 g (10.0 mmole) of 2-aminobenzoxazole, 1.56 g (10.0 mmole) of ethyl tetrazol-5-ylacetate, 1.65 g (11.1 mmole) of triethyl orthoformate and 0.3 g (2.2 mmole) of aluminum trichloride in 25 ml of 1,1,2,2-tetrachloroethane was heated under a nitrogen atmosphere at 125° to 130° C. for about 19 hours. The mixture was cooled and the resulting solid was separated by filtration and washed with methanol to provide 0.72 g (28%) of crude-3-(1H-tetrazol-5-yl)-4H-pyrimido[2,1-b]benzoxazol-4-one. Infrared spectral analysis of the crude product showed that it was the desired product.

EXAMPLE 5

Alternative Synthesis of 3-(1H-Tetrazol-5-yl)-4H-pyrimido[2,1-b]benzothiazol-4-one A mixture of 1.50 g (10.0 mmole) of 2-aminobenzothiazole, 1.56 g (10.0 mmole) of ethyl tetrazol-5-ylacetate, 1.70 g (11.5 mmole) of triethyl orthoformate and 0.3 g (2.2 mmole) of aluminum trichloride in 25 ml of 1,1,2,2-tetrachloroethane was heated at 130° C. for about 18 hours. The mixture was cooled and the solid was separated by filtration and washed with methanol to provide 2.51 g (93%) of a light yellow solid. Infrared and nuclear magnetic resonance spectral analyses of this crude product confirmed that it was 3-(1H-tetrazol-5-yl)-4H-pyrimido[2,1-b]benzothiazol-4-one of good purity.

EXAMPLE 6

Alternative Synthesis of 6-(1H-Tetrazol-5-yl)thiazolo[3,2-a]pyrimidine-5-one

A mixture of 1.00 g (10.0 mmole) of 2-aminothiazole, 1.56 g (10.0 mmole) of ethyl tetrazol-5-ylacetate, 1.74 g (11.8 mmole) of triethyl orthoformate and 0.3 g (2.2 mmole) of aluminum chloride in 50 ml of 1,1,2,2-tetrachlorethane was heated at 120° C. for about 18 hours under a nitrogen atmosphere. The mixture was cooled, diluted to 200 ml with diethyl ether and filtered. The solid was suspended and stirred in 50 ml of 1:1 methanol-water and then filtered and washed with methanol to provide 1.49 g (68%) of brownish-colored solid 6-(1H-tetrazol-5-yl)thiazolo[3,2-a]pyrimidin-4-one. Infrared spectral analysis indicated that the product was impure. The product was suspended in 30 ml of N,N-dimethylformamide and the resulting mixture was heated to boiling, cooled and filtered. The solid obtained was stirred into 60 ml of boiling water, and the mixture was filtered while hot. The solid recovered was washed with methanol, stirred in 20 ml of boiling N,N-dimethylformamide, and recovered by filtration. The resulting solid was then washed sequentially with hot water and methanol and then dried to provide 0.74 g (34%) of a gray solid. The infrared spectrum of this product confirmed its purity.

EXAMPLE 7

Synthesis of Ethyl 2-[N-(2-Benzothiazolyl)-amino]-1-(1-H-tetrazol-5-yl)acrylate in Dioxane.

A mixture of 1.50 g (10.0 mmole) of 2-aminobenzothiazole, 1.56 g (10.0 mmole) of ethyl tetrazol-5-ylacetate, 1.70 g (11.5 mmole) of triethyl orthoformate, 0.3 g (2.2 mmole) of aluminum chloride and 40 ml of dioxane was heated at reflux overnight. The mixture was then cooled, poured into 200 ml of water and acidified with one milliliter of concentrated hydrochloric acid. The precipitated solid was separated by filtration and washed sequentially with water and methanol. The product, a fluffy, light yellow solid, was 1.87 g (59%) of ethyl 2-[N-(2-benzothiazolyl)amino]-1-(1H-tetrazol-5-yl)acrylate. Infrared spectral analysis of the product confirmed that it was the intermediate of Example 1.

EXAMPLE 8–25

The following Table (1) describes several compounds of Formula I which may be made by following Procedure A of the invention and employing ethyl tetrazol-5-yl-acetate as the alkyl tetrazol-5-yl-acetate of Formula III. Table (1) indicates the known starting material which may be used to prepare each compound. The novel intermediates of Formula IV which are formed in Procedure A are also described in Table (1). The compounds of Formula I described below may also be prepared from the indicated starting material via Procedure B of the invention. When Procedure B is followed, the intermediate of Formula IV is not isolated.

TABLE I

| EXAMPLE NUMBER | STARTING MATERIAL OF FORMULA II | INTERMEDIATE OF FORMULA II | FINAL PRODUCT OF FORMULA I |
|---|---|---|---|
| 8 | (2-aminooxazole) | | |
| 9 | (2-amino-4,5-dimethyl-oxazole) | | |
| 10 | (2-amino-5-chlorobenzoxazole) | | |
| 11 | (2-amino-5-methoxybenzoxazole) | | |

TABLE I-continued
| EXAMPLE NUMBER | STARTING MATERIAL OF FORMULA II | INTERMEDIATE OF FORMULA II | FINAL PRODUCT OF FORMULA I |
|---|---|---|---|
| 12 | (2-amino-6-chloro-benzoxazole) | | |
| 13 | (2-amino-5-methyl-benzoxazole) | | |
| 14 | (2-amino-7-chloro-benzoxazole) | | |
| 15 | (2-amino-4-chloro-benzoxazole) | | |
| 16 | (2-amino-5,6-dichloro-benzoxazole) | | |
| 17 | (2-amino-4,5-dimethylthiazole) | | |
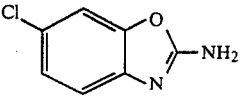

TABLE I-continued
| EXAMPLE NUMBER | STARTING MATERIAL OF FORMULA II | INTERMEDIATE OF FORMULA II | FINAL PRODUCT OF FORMULA I |
|---|---|---|---|
| 18 | 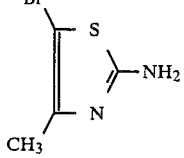<br>(2-amino-4-methyl-5-bromothiazole) | 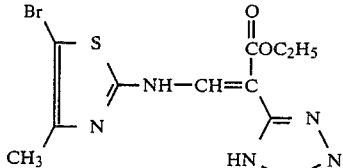 | 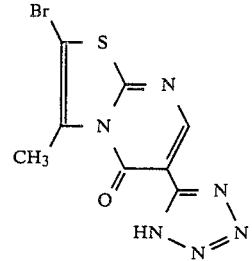 |
| 19 | 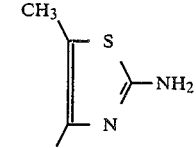<br>(2-amino-4-methoxy-5-methylthiazole) | 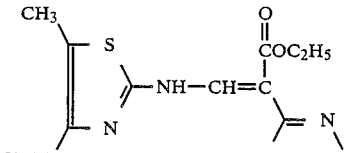 | 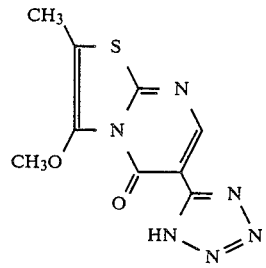 |
| 20 | 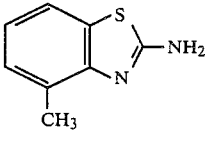<br>(2-amino-4-methyl-benzothiazole) | 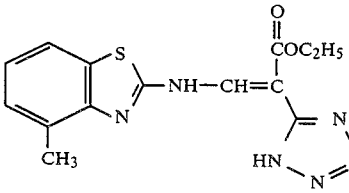 | 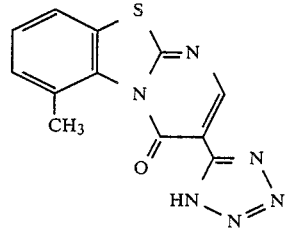 |
| 21 | 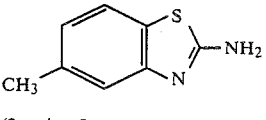<br>(2-amino-5-methylbenzothiazole) | 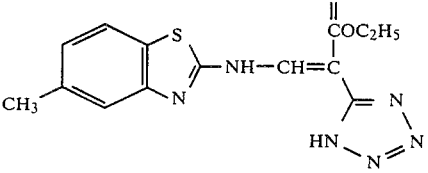 | 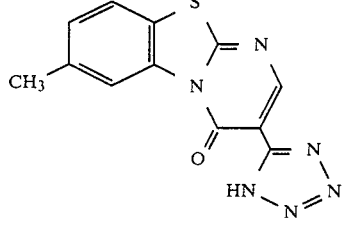 |
| 22 | 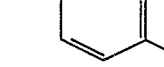<br>(2-amino-6-methyl-benzothiazole) | 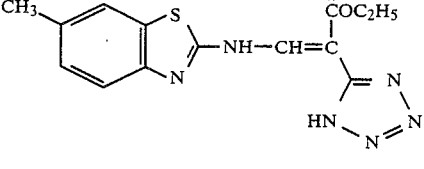 | 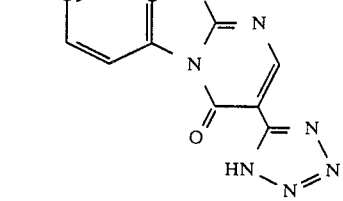 |
| 23 | 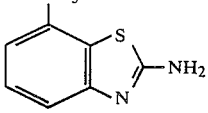<br>(2-amino-7-methyl-benzothiazole) | 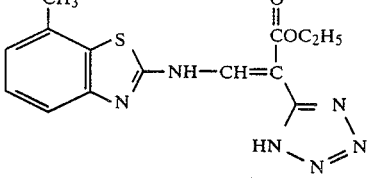 | 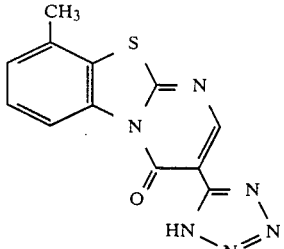 |

TABLE I-continued

| EXAMPLE NUMBER | STARTING MATERIAL OF FORMULA II | INTERMEDIATE OF FORMULA II | FINAL PRODUCT OF FORMULA I |
|---|---|---|---|
| 24 | (2-amino-5,6-dimethoxybenzothiazole) | | |
| 25 | (2-amino-4-chlorobenzothiazole) | | |
| 26 | (2-amino-4-chlorooxazole) | | |

What is claimed is:

1. A process for the preparation of a compound of the formula

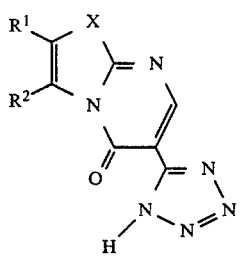

wherein X is sulfur or oxygen and $R^1$ and $R^2$ are independently selected from the group consisting of H and an alkyl group containing 1 to about 4 carbon atoms, or $R^1$ and $R^2$ are fused to form an unsubstituted benzene ring or a substituted benzene ring having one or more substituents independently from the group consisting of an alkyl group containing 1 to about 4 carbon atoms, an alkoxy group containing 1 to about 4 carbon atoms, and halogen comprising (1) reacting together a heterocyclic amine of the formula

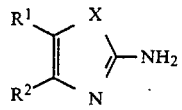

wherein X, $R^1$ and $R^2$ are as defined above, an alkyl tetrazol-5-ylacetate of the formula

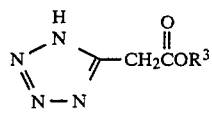

wherein $R^3$ is an alkyl group containing 1 to about 4 carbon atoms, and a trialkyl orthoformate of the formula

wherein $R^4$ is an alkyl group containing 1 to about 4 carbon atoms, in the presence of a Lewis acid to provide a 2-(N-heterocyclyl)-amino-1-(1H-tetrazol-5-yl)acrylate ester, and (2) condensing the 2-(N-heterocyclyl)amino-1-(1H-tetrazol-5-yl)acrylate ester in the presence of polyphosphoric acid.

2. A process for the preparation of a compound of the formula

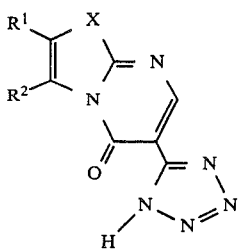

wherein X is sulfur or oxygen and $R^1$ and $R^2$ are independently selected from the group consisting of H and an alkyl group containing 1 to about 4 carbon atoms, or $R^1$ and $R^2$ are fused to form an unsubstituted benzene ring or a substituted benzene ring having one or more substituents independently selected from the group consisting of an alkyl group containing 1 to about 4 carbon atoms, an alkoxy group containing 1 to about 4 carbon atoms and halogen, comprising reacting together a heterocyclic amine of the formula

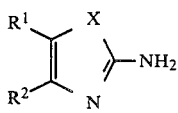

wherein X, $R^1$ and $R^2$ are as defined above, an alkyl tetrazol-5-ylacetate of the formula

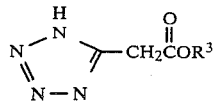

wherein $R^3$ is an alkyl group containing 1 to about 4 carbon atoms, and a trialkyl orthoformate of the formula

wherein $R^4$ is an alkyl group containing 1 to about 4 carbon atoms, in the presence of a Lewis acid and 1,1,2,2-tetrachloroethane.

3. A process in accordance with claim 1 or 2, wherein said trialkyl orthoformate is selected from the group consisting of trimethyl orthoformate and triethyl orthoformate.

4. A process in accordance with claim 1 or 2, wherein said Lewis acid is aluminum trichloride.

5. A process in accordance with claim 1 or 2, wherein said heterocyclic amine is selected from the group consisting of a 2-aminooxazole and a 2-aminobenzoxazole.

6. A process in accordance with claim 1 or 2, wherein said heterocyclic amine is selected from the group consisting of a 2-aminothiazole and a 2-aminobenzothiazole.

* * * * *